United States Patent
Pagotto Simões et al.

(10) Patent No.: US 9,686,997 B2
(45) Date of Patent: Jun. 27, 2017

(54) ANTIMICROBIAL COMPOSITIONS AND USES THEREOF

(75) Inventors: Luiz Gustavo Pagotto Simões, São Carlos/SP (BR); Andre Luiz De Araújo, São Carlos/SP (BR); Daniel Tamassia Minozzi, Sao Cãrlos/SP (BR)

(73) Assignee: NANOX TECHNOLOGY LLC, Newton, MA (US)

( * ) Notice: Subject to any disclaimer, the term of this patent is extended or adjusted under 35 U.S.C. 154(b) by 0 days.

(21) Appl. No.: 14/342,455

(22) PCT Filed: Sep. 6, 2012

(86) PCT No.: PCT/BR2012/000337
§ 371 (c)(1),
(2), (4) Date: Mar. 3, 2014

(87) PCT Pub. No.: WO2013/033802
PCT Pub. Date: Mar. 14, 2013

(65) Prior Publication Data
US 2014/0220153 A1    Aug. 7, 2014

Related U.S. Application Data

(60) Provisional application No. 61/532,345, filed on Sep. 8, 2011.

(51) Int. Cl.
| | |
|---|---|
| *A01N 59/16* | (2006.01) |
| *A61K 33/38* | (2006.01) |
| *A61K 33/30* | (2006.01) |
| *A61K 33/08* | (2006.01) |
| *A61K 33/24* | (2006.01) |
| *A61K 33/34* | (2006.01) |

(52) U.S. Cl.
CPC ............ *A01N 59/16* (2013.01); *A61K 33/08* (2013.01); *A61K 33/24* (2013.01); *A61K 33/30* (2013.01); *A61K 33/34* (2013.01); *A61K 33/38* (2013.01)

(58) Field of Classification Search
None
See application file for complete search history.

(56) References Cited

U.S. PATENT DOCUMENTS

| | | | | |
|---|---|---|---|---|
| 4,906,466 A * | 3/1990 | Edwards | ................ | A01N 59/16 424/421 |
| 5,180,585 A * | 1/1993 | Jacobson | ................ | A01N 25/26 424/404 |
| 6,013,275 A | 1/2000 | Konagaya et al. | | |
| 7,641,912 B1 | 1/2010 | Redler | | |
| 2003/0032765 A1 | 2/2003 | McDonald et al. | | |
| 2005/0124724 A1 | 6/2005 | Burton et al. | | |
| 2007/0207335 A1 * | 9/2007 | Karandikar | ................ | H01B 1/02 428/560 |
| 2007/0208102 A1 | 9/2007 | Reynaud et al. | | |
| 2009/0252699 A1 | 10/2009 | Kocher et al. | | |

FOREIGN PATENT DOCUMENTS

| | | |
|---|---|---|
| EP | 1159972 A2 | 12/2001 |
| EP | 1329211 A1 | 7/2003 |
| EP | 1374830 A1 | 1/2004 |
| GB | 2464610 A | 4/2010 |
| JP | H08119821 A | 5/1996 |
| WO | 03/051278 A2 | 6/2003 |
| WO | 2005/014074 A1 | 2/2005 |
| WO | 2005/087855 A1 | 9/2005 |
| WO | 2007/085852 A2 | 8/2007 |
| WO | 2008089822 A2 | 7/2008 |

OTHER PUBLICATIONS

Alexandre et al., "Polymer-layered silicate noncomposites: preparation, properties and uses of a new class of materials", Materials Science and Engineering 28:1-63 (2000).
Canamares et al., "Comparative Study of the Morphology, Aggregation, Adherence to Glass, and Surface-Enhanced Raman Scattering Activity of Silver Nanoparticles Prepared by Chemical Reduction of Ag+ Using Citrate and Hydroxylamine", Langmuir 21(18):8546-8553 (2005).
Frost et al. "Strategic Analysis of the European Plastic Packaging Additives Market" M193-39. (2009).
Leite, "Nanocrystals Assembled from the Bottom Up", In: Encyclopedia of Nanoscience and Nanotechnology, NALWA (Ed), Washington: American Scientific Publishers 6:537-554 (2004).
Sheng et al., "Sedimentation Classification of Silver Colloids for Surface-Enhanced Raman Scattering", Anal. Chem. 58:1116-1119 (1986).
Sinha Ray et al., "Polymer/layered silicate nanocomposites: a review from preparation to processing", Prog. Polym. Sci. 28:1539-1641 (2003).
Miyasato et al. "A newly developed wound dressing made of alginate fiber containing zeolite substituted by silver and zinc: Fundamental study," Yakuri To Chiryo (1999) 27(4), 177-203 (English Abstract only).
Miyasato et al., "A Newly Developed Wound Dressing Made of Alginate Fiber Containing Zeolite Substituted by Silver and Zinc:Fundamental Study", Japanese Pharmacology and Therapeutics 27(4):177-204 (1999).

\* cited by examiner

*Primary Examiner* — Robert A Wax
*Assistant Examiner* — Quanglong Truong
(74) *Attorney, Agent, or Firm* — Nixon Peabody LLP

(57) ABSTRACT

The invention is generally directed to antimicrobial composition comprising a matrix material and both of silver and zinc distributed there through, wherein the matrix material comprises at least one of $SiO_2$, $TiO_2$, $ZrO_2$, $Al_2O_3$, or Zeolite, and the uses of such compositions as antibacterial and acaricidal. The invention is also generally directed to antimicrobial composition comprising a matrix material arid both of silver and a metal selected from the group of noble or transition metals distributed there through, wherein the matrix material comprises at least one of $SiO_2$, $TiO_2$, $ZrO_2$, $Al_2O_3$, or Zeolite, and the uses of such compositions as antibacterial and acaricidal.

28 Claims, 2 Drawing Sheets

ANTIMICROBIAL COMPOSITIONS AND USES THEREOF

CROSS REFERENCE TO RELATED APPLICATIONS

This application is a 35 U.S.C. §371 National Phase Entry Application of International Application No. PCT/BR2012/000337 filed Sep. 6, 2012, which designates the U.S., and which claims benefit under 35 U.S.C. §119(e) of U.S. Provisional Patent Application Ser. No. 61/532,345 filed on Sep. 8, 2011, the contents of each of which are herein incorporated by reference in their entireties.

FIELD OF THE INVENTION

The invention relates generally to natural silver-based composition with bactericidal, acaricidal, antifungal, and antiviral properties as well as activity against various microorganisms. The invention also relates to the composition being a particle and the uses of such.

BACKGROUND OF THE INVENTION

Nanotechnology comprises technological developments within the nanometer scale (between 1 and 100 nm). Interdisciplinary, it falls within the field of nanoscience and turned to its advances, which involves physics, chemistry, engineering, computer science, biology and environmental sciences. Governed by the laws of quantum physics, the universe of nanoparticles may cause materials to present different behaviors in the nanoscale than shown in the normal macro and microscopic scale. For example, some materials that are naturally opaque or translucent to the naked eye exhibit transparent behavior at the nanoscale. Some materials are known as "smart materials", since their new properties under the treatment of nanotechnology can be combined with their original attributes, to play multiple or adaptive functions, such as by enabling the interfacing of organic and inorganic materials (Leite, E. R. Nanocrystals assembled from the bottom up. In: NALWA, H. S. (Ed.). Encyclopedia of nanoscience and nanotechnology. Washington: American Scientific Publishers, 2004. v. 6, p. 537-554).

Nanomaterials by definition have at least one dimension in the nanometer scale. Currently being added to polymers, nanomaterials aim at stimulating changes in the physical, chemical and mechanical polymeric behaviors, or to confer entirely new properties to polymers (M. Alexandre, P. Dubois Materials Science and Engineering 28 (2000) 1±63; S. Sinha Ray, M. Okamoto Prog. Polym. Sci. 28 (2003) 1539-1641). As a practical matter, it can be highlighted that the use of antimicrobial additives to induce bactericidal and/or fungicidal properties to polymers can promote:
  Total or partial elimination of the harmful effects of microbes in healthcare, including prevention of new, virulent mutations that may pose health risks and/or reduce the longevity of the products;
  Effective sterilization, promoting cleaner products and environments, helping to prevent diseases and supporting preventive health and wellness. Sterilization also avoids the formation of mold and other causes of unpleasant odors, improving surface cleanliness and reduction of the maintenance costs;
  Improvement of strategies used by the food industry to sustain or increase product shelf life; examples are enhanced antimicrobial containers that keep the original food flavor, leading to healthier products that also preserve the original food properties.

Types of Antimicrobial Additives

Antimicrobial additives may be classified as natural or chemical. Natural additives are inorganic, silver-based compounds, such as a core of oxides, halides and glass particles (silica, titania, zeolite), coated with silver-based compounds. Chemical additives, on the other hand, are based on compounds such as chlorophenol and thiabendazole (Frost & Sullivan. Strategic Analysis of the European Plastic Packaging Additives Market M193-39. April 2009).

There is a current trend towards the use of natural silver-based antimicrobial additives over the, chemical ones, mainly for two reasons:
  Organic chemical additives represent a possible health threat;
  The development of resistance in bacteria seems more closely related to organic chemical additives than to natural ones.

Organic antimicrobial chemical additives are more prone to leaching than silver-based additives, leading to a reduction of its effectiveness or even efficacy (functionality). There is a concern that if chemical additives are used in applications such as containers for food packaging, they may migrate into the food. Chlorophenol, for example, has been detected in breast milk after use in food packaging, also raising concerns about a possible role of this chemical additive in the development of cancer.

Natural silver-based compounds have the major advantage of being static, generally not subjected to leaching, with a solid and lasting effect throughout the product's life. In the unlikely event that a silver-based additive does migrate from the container to the surface of the product, they should not represent a significant health risk, since they are nontoxic, inert and non-corrosive.

Throughout the ages, silver has been used for applications where a sterile environment is required. It is known to be safe, odorless, and highly effective. As a result, the silver-based are the most used antimicrobial additives by the plastic packaging industry. Unlike organic additives, silver is also rarely associated with the onset of resistance in microorganisms.

On the manufacturing side, silver-based antimicrobials display heat stability, being stable up to about 800° C. They can be processed at high temperatures and incorporated into polymers prior to processing, even at high processing temperature. Organic antimicrobials may decompose under high temperatures.

Natural silver-based compounds maintain its bactericidal efficacy in aqueous media, leading to a higher longevity (service life) than organic additives. As a declaration of its non-toxicity and high efficacy, silver-based antimicrobial additives are the additives of choice by healthcare organizations. Organic additives have also been under observation because of safety concerns, and impending regulations may restrict their use in the future, especially in uses like food packaging.

Historically, silver has been used as an effective treatment, against hundreds of infectious conditions, due to the selective effect of the silver ions on microorganisms (bacteria, fungi, viruses). This effect is through at least three distinct mechanisms: (1) transport functions in the cell wall (respiration); (2) cell division (reproduction); and (3) generation of energy (metabolism). The negative effect of silver on these vital functions leads to a growth inhibition in microorganisms, the so-called bacteriostatic effect. For bacteria, it also prevents the colonization of other, different but related bacterial strains.

Silver-based compounds can either be (1) attached directly to a surface, by complexing them with a given polymer, or (2) anchored to a surface by prior impregnation to a ceramic particle (silica, zeolite, titania), before incorporation into the polymer.

Several methods have been developed to prepare silver nanoparticles, including chemical reduction, laser ablation and photoreduction, but chemical reactions in solution (wet chemistry) is the most commonly used. Classic wet chemistry methods typically start by first mixing metal salts, which are then reduced by a chemical agent to produce colloidal suspensions which then result in metal nanoparticles [6]. Sodium borohydride and trisodium citrate have been widely used as reducing agents. Both are proven to produce monodisperse colloids with size and desired characteristics (M. V. Canamares, J. V. Garcia-Ramos, J. D. Gomez-Varga, C. Domingo, S. Sanches-Cortes, Langmuir, 21, 2005, pp. 8546-8553; R. S. Sheng, L. Zhu, M. D. Morris, Anal. Chem., 58, 1986, pp. 1116-1119).

Nanotechnology-based antimicrobial additives have a superior bacteriostatic effect, since their high surface makes up for a relatively large contact area between their active component, silver, and the microorganism surface. This allows lower concentrations of antimicrobial nanoadditives to be used, as compared to additives in higher scales, such as the micrometer scale.

SUMMARY OF THE INVENTION

The invention is generally directed to antimicrobial composition comprising a matrix material and both of silver and zinc distributed there through, wherein the matrix material comprises at least one of $SiO_2$, $TiO_2$, $ZrO_2$, $Al_2O3$, or Zeolite, and the uses of such compositions as antibacterial and acaricidal. The invention is also generally directed to antimicrobial composition comprising a matrix material and both of silver and a metal selected from the group of noble or transition metals distributed there through, wherein the matrix material comprises at least one of $SiO_2$, $TiO_2$, $ZrO_2$, $Al_2O3$, or Zeolite, and the uses of such compositions as antibacterial and acaricidal.

One aspect of the invention provides antimicrobial compositions comprising a matrix material and both of silver and zinc distributed there through, wherein the matrix material comprises at least one of $SiO_2$, $TiO_2$, $ZrO_2$, $Al_2O_3$, or Zeolite.

One aspect of the invention provides a composition of the invention, wherein the composition possesses antibacterial activity.

One aspect of the invention provides a composition of the invention, wherein the composition possesses acaricidal activity.

One aspect of the invention provides a composition of the invention, wherein the composition posses antifungal, antiviral, or antiparasitical activity.

One aspect of the invention, provides a composition of the invention, wherein the composition posses activity against other types of microorganisms.

One aspect of the invention provides a polymer comprising a composition of the invention.

One aspect of the invention provides a molded article comprising a composition of the invention.

One aspect of the invention provides a nanofiller comprising a composition of the invention.

One aspect of the invention provides a ceramic glaze comprising a composition of the invention.

One aspect of the invention provides a plastic resin comprising a composition of the invention.

One aspect of the invention provides an antimicrobial solution comprising a composition of the invention.

One aspect of the invention provides an acaricidal solution comprising a composition of the invention.

DEFINITIONS

Before further description of the present invention, and in order that the invention may be more readily understood, certain terms are first defined and collected here for convenience. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with number can mean within ±1% of that number.

The term "antimicrobial activity" refers to the ability of a compound of the present invention to inhibit or kill at least one species selected from the group consisting of bacteria, fungi, parasite, protozoans, viruses, algae, or mites. In general, it is preferred that the compound inhibits or kills at least, 50%, 60%, 70%, 90% or all cells of at least one species of bacteria, fungi, parasite, protozoans, viruses, algae, or mites.

The term "nanofiller" refers to substances with the ability to disperse in the matrix polymer in such a way that structures in the nanoscale (1-100 nm) are obtained.

The term "nanoadditive" refers to a nanocomposite of clay in a polymer or copolymer where silicate is dispersed in a matrix of polymer or copolymer.

BRIEF DESCRIPTION OF THE DRAWINGS

FIG. 2A shows a scanning electronic microscopy (SEM) image of a sample with 0.5 wt % Ag and Zn, where the silver and zinc metals are dispersed on the $SiO_2$ matrix. FIG. 2B shows a schematic representation of the microstructure of the silver-based additive, with the metal nanoparticles dispersed on the $SiO_2$ matrix.

DETAILED DESCRIPTION OF THE INVENTION

The invention described herein is based, in part, on the discovery of a new silver-based composition that possesses antimicrobial activity. An important aspect of the invention is the novel antimicrobial compositions are non-toxic. In that regard, the use of the composition of the invention are numerous and widely varied, for example from its use in textile, building material, cleaners, various polymers, resins, etc and its incorporation in food containers or in food applications.

Accordingly, the invention provides compounds, compositions and solutions comprising a matrix material and both of silver and zinc distributed there through, wherein the matrix material comprises at least one oxide. Without wishing to be bound by a theory, addition of Zn provides enhanced properties such as increased antimicrobial activity. In some embodiments, the oxide is selected from the group consisting of $SiO_2$, $TiO_2$, $ZrO_2$, $Al_2O_3$, or Zeolite.

One aspect of the invention provides antimicrobial compositions comprising a matrix material and both of silver and zinc distributed there through, wherein the matrix material comprises at least one of $SiO_2$, $TiO_2$, $ZrO_2$, $Al2O_3$, or Zeolite. In some embodiments, antimicrobial is antibacterial. In some embodiments, antimicrobial is acaricidal. In some embodiments, antimicrobial is antifungal. In some embodiments, antimicrobial is antiviral. In some embodiments, antimicrobial is antiparasitical. In some embodiments, antimicrobial is antimicrobial against other types of microorganisms.

In some embodiments, the composition comprises an additional material, also referred to as non-matrix material. Compositions The compositions of the instant invention comprise a matrix material and both silver and zinc distributed there through, wherein the matrix material comprises at least one oxide.

Other compositions of the instant invention comprise a matrix material, and both silver and at least one element selected from the group consisting of noble and transition metals, wherein the matrix material comprises at least one oxide.

In some embodiments, element selected from the group consisting of noble and transition metals is a noble metal. In some embodiments, element selected from the group consisting of noble and transition metals is a transition metal. In some embodiments, element selected from the group consisting of noble and transition metals is Pd, Rh, Ru, Cu, or Au.

In some embodiments, the oxide is selected from the group consisting of $SiO_2$, $TiO_2$, $ZrO_2$, $Al_2O_3$, or Zeolite. In some embodiments, the oxide is $SiO_2$. In some embodiments, the oxide is TiO2. In some embodiments, the oxide is $ZrO_2$. In some embodiments, the oxide is $Al_2O_3$. In some embodiments, the oxide is Zeolite.

In certain aspects of the invention, the composition further comprises at least one a metal selected from the group consisting of noble metals, transitions metals and any combinations thereof. In certain aspects of the invention, the composition further comprises at least one metal selected from the group consisting of Cu, Pt, Rh, Ni, Co, Ru, and any combinations thereof. In certain aspects of the invention, the composition further comprises only one metal selected from the group consisting of noble metals, and transition metals. In some embodiments, the composition further comprises only one metal selected from the group consisting of Cu, Pt, Rh, Ni, Co, and Ru. In some embodiments, the composition further comprises at least one metal selected from the group consisting of Cu, Pt, Rh, Ni, Co, and Ru. In some embodiments, the composition further comprises at least two metal selected from the group consisting of Cu, Pt, Rh, Ni, Co, and Ru. In some embodiments, the composition further comprises at least three metal selected from the group consisting of Cu, Pt, Rh, Ni, Co, and Ru. In some embodiments, the composition further comprises at least four metal selected from the group consisting of Cu, Pt, Rh, Ni, Co, and Ru. In some embodiments, the composition further comprises at least five metal selected from the group consisting of Cu, Pt, Rh, Ni, Co, and Ru. In some embodiments, the composition further comprises at least six metal selected from the group consisting of Cu, Pt, Rh, Ni, Co, and Ru. In some embodiments, the composition further comprises Cu, Pt, Rh, Ni, Co, and Ru.

Certain aspects of the invention relate to the amount of certain component of the composition of the invention.

In some embodiments, the composition comprises from about 0.05% to about 10% Ag. In some embodiments, the composition comprises from about 0.1% to about 5% Ag. In some embodiments, the composition comprises from about 5% to about 10% Ag. In some embodiments, the composition comprises at least 10% Ag. In some embodiments, the composition comprises about 0.1% Ag. In some embodiments, the composition comprises about 0.2% Ag. In some embodiments, the composition comprises 0.3% Ag. In some embodiments, the composition comprises 0.4% Ag. In some embodiments, the composition comprises about 0.5% Ag. In some embodiments, the composition comprises about 0.6% Ag. In some embodiments, the composition comprises 0.7% Ag. In some embodiments, the composition comprises 0.8% Ag. In some embodiments, the composition comprises about 0.9% Ag. In some embodiments, the composition comprises about 1% Ag. In some embodiments, the composition comprises about 2% Ag. In some embodiments, the composition comprises about 3% Ag. In some embodiments, the composition comprises about 4% Ag. In some embodiments, the composition comprises about 5% Ag. In some embodiments, the composition comprises about 6% Ag. In some embodiments, the composition comprises about 7% Ag. In some embodiments, the composition comprises about 8% Ag. In some embodiments, the composition comprises about 9% Ag. In some embodiments, the composition comprises about 10% Ag.

In some embodiments, the composition comprises from about 0.05% to about 10% Zn. In some embodiments, the composition comprises from about 0.1% to about 5% Zn. In some embodiments, the composition comprises from about 5% to about 10% Zn. In some embodiments, the composition comprises at least 10% Zn. In some embodiments, the composition comprises about 0.1% Zn. In some embodiments, the composition comprises about 0.2% Zn. In some embodiments, the composition comprises 0.3% Zn. In some embodiments, the composition comprises 0.4% Zn. In some embodiments, the composition comprises about 0.5% Zn. In some embodiments, the composition comprises about 0.6% Zn. In some embodiments, the composition comprises 0.7% Zn. In some embodiments, the composition comprises 0.8% Zn. In some embodiments, the composition comprises about 0.9% Zn. In some embodiments, the composition comprises about 1% Zn. In some embodiments, the composition comprises about 2% Zn. In some embodiments, the composition comprises about 3% Zn. In some embodiments, the composition comprises about 4% Zn. In some embodiments, the composition comprises about 5% Zn. In some embodiments, the composition comprises about 6% Zn. In some embodiments, the composition comprises about 7% Zn. In some embodiments, the composition comprises about 8% Zn. In some embodiments, the composition comprises about 9% Zn. In some embodiments, the composition comprises about 10% Zn.

In some embodiments, the composition comprises from about 0.05% to about 10% Cu. In some embodiments, the composition comprises from about 0.1% to about 5% Cu. In some embodiments, the composition comprises from about 5% to about 10% Cu. In some embodiments, the composition comprises at least 10% Cu. In some embodiments, the composition comprises about 0.1% Cu. In some embodiments, the composition comprises about 0.2% Cu. In some embodiments, the composition comprises 0.3% Cu. In some embodiments, the composition comprises 0.4% Cu. In some embodiments, the composition comprises about 0.5% Cu. In some embodiments, the composition comprises about 0.6% Cu. In some embodiments, the composition comprises 0.7% Cu. In some embodiments, the composition comprises 0.8% Cu. In some embodiments, the composition comprises about 0.9% Cu. In some embodiments, the composition comprises about 1% Cu. In some embodiments, the composition comprises about 2% Cu. In some embodiments, the composition comprises about 3% Cu. In some embodiments, the composition comprises about 4% Cu. In some embodiments, the composition comprises about 5% Cu. In some embodiments, the composition comprises about 6% Cu. In some embodiments, the composition comprises about 7% Cu. In some embodiments, the composition comprises about 8% Cu. In some embodiments, the composition comprises about 9% Cu. In some embodiments, the composition comprises about 10% Cu.

In some embodiments, the composition comprises from about 0.05% to about 10% Pt. In some embodiments, the composition comprises from about 0.1% to about 5% Pt. In some embodiments, the composition comprises from about 5% to about 10% Pt. In some embodiments, the composition comprises at least 10% Pt. In some embodiments, the composition comprises about 0.1% Pt. In some embodiments, the composition comprises about 0.2% Pt. In some embodiments, the composition comprises 0.3% Pt. In some embodiments, the composition comprises 0.4% Pt. In some embodiments, the composition comprises about 0.5% Pt. In some embodiments, the composition comprises about 0.6% Pt. In some embodiments, the composition comprises 0.7% Pt. In some embodiments, the composition comprises 0.8% Pt. In some embodiments, the composition comprises about 0.9% Pt. In some embodiments, the composition comprises about 1% Pt. In some embodiments, the composition comprises about 2% Pt. In some embodiments, the composition comprises about 3% Pt. In some embodiments, the composition comprises about 4% Pt. In some embodiments, the composition comprises about 5% Pt. In some embodiments, the composition comprises about 6% Pt. In some embodiments, the composition comprises about 7% Pt. In some embodiments, the composition comprises about 8% Pt. In some embodiments, the composition comprises about 9% Pt. In some embodiments, the composition comprises about 10% Pt.

In some embodiments, the composition comprises from about 0.05% to about 10% Rh. In some embodiments, the composition comprises from about 0.1% to about 5% Rh. In some embodiments, the composition comprises from about 5% to about 10% Rh. In some embodiments, the composition comprises at least 10% Rh. In some embodiments, the composition comprises about 0.1% Rh. In some embodiments, the composition comprises about 0.2% Rh. In some embodiments, the composition comprises 0.3% Rh. In some embodiments, the composition comprises 0.4% Rh. In some embodiments, the composition comprises about 0.5% Rh. In some embodiments, the composition comprises about 0.6% Rh. In some embodiments, the composition comprises 0.7% Rh. In some embodiments, the composition comprises 0.8% Rh. In some embodiments, the composition comprises about 0.9% Rh. In some embodiments, the composition comprises about 1% Rh. In some embodiments, the composition comprises about 2% Rh. In some embodiments, the composition comprises about 3% Rh. In some embodiments, the composition comprises about 4% Rh. In some embodiments, the composition comprises about 5% Rh. In some embodiments, the composition comprises about 6% Rh. In some embodiments, the composition comprises about 7% Rh. In some embodiments, the composition comprises about 8% Rh. In some embodiments, the composition comprises about 9% Rh. In some embodiments, the composition comprises about 10% Rh.

In some embodiments, the composition comprises from about 0.05% to about 10% Ni. In some embodiments, the composition comprises from about 0.1% to about 5% Ni. In some embodiments, the composition comprises from about 5% to about 10% Ni. In some embodiments, the composition comprises at least 10% Ni. In some embodiments, the composition comprises about 0.1% Ni. In some embodiments, the composition comprises about 0.2% Ni. In some embodiments, the composition comprises 0.3% Ni. In some embodiments, the composition comprises 0.4% Ni. In some embodiments, the composition comprises about 0.5% Ni. In some embodiments, the composition comprises about 0.6% Ni. In some embodiments, the composition comprises 0.7% Ni. In some embodiments, the composition comprises 0.8% Ni. In some embodiments, the composition comprises about 0.9% Ni. In some embodiments, the composition comprises about 1% Ni. In some embodiments, the composition comprises about 2% Ni. In some embodiments, the composition comprises about 3% Ni. In some embodiments, the composition comprises about 4% Ni. In some embodiments, the composition comprises about 5% Ni. In some embodiments, the composition comprises about 6% Ni. In some embodiments, the composition comprises about 7% Ni. In some embodiments, the composition comprises about 8% Ni. In some embodiments, the composition comprises about 9% Ni. In some embodiments, the composition comprises about 10% Ni.

In some embodiments, the composition comprises from about 0.05% to about 10% Co. In some embodiments, the composition comprises from about 0.1% to about 5% Co. In some embodiments, the composition comprises from about 5% to about 10% Co. In some embodiments, the composition comprises at least 10% Co. In some embodiments, the composition comprises about 0.1% Co. In some embodiments, the composition comprises about 0.2% Co. In some embodiments, the composition comprises 0.3% Co. In some embodiments, the composition comprises 0.4% Co. In some embodiments, the composition comprises about 0.5% Co. In some embodiments, the composition comprises about 0.6% Co. In some embodiments, the composition comprises 0.7% Co. In some embodiments, the composition comprises 0.8% Co. In some embodiments, the composition comprises about 0.9% Co. In some embodiments, the composition comprises about 1% Co. In some embodiments, the composition comprises about 2% Co. In some embodiments, the composition comprises about 3% Co. In some embodiments, the composition comprises about 4% Co. In some embodiments, the composition comprises about 5% Co. In some embodiments, the composition comprises about 6% Co. In some embodiments, the composition comprises about 7% Co. In some embodiments, the composition comprises about 8% Co. In some embodiments, the composition comprises about 9% Co. In some embodiments, the composition comprises about 10% Co.

In some embodiments, the composition comprises from about 0.05% to about 10% Ru. In some embodiments, the composition comprises from about 0.1% to about 5% Ru. In some embodiments, the composition comprises from about 5% to about 10% Ru. In some embodiments, the composition comprises at least 10% Ru. In some embodiments, the composition comprises about 0.1% Ru. In some embodiments, the composition comprises about 0.2% Ru. In some embodiments, the composition comprises 0.3% Ru. In some embodiments, the composition comprises 0.4% Ru. In some embodiments, the composition comprises about 0.5% Ru. In some embodiments, the composition comprises about 0.6% Ru. In some embodiments, the composition comprises 0.7% Ru. In some embodiments, the composition comprises 0.8% Ru. In some embodiments, the composition comprises about 0.9% Ru. In some embodiments, the composition comprises about 1% Ru. In some embodiments, the composition comprises about 2% Ru. In some embodiments, the composition comprises about 3% Ru. In some embodiments, the composition comprises about 4% Ru. In some embodiments, the composition comprises about 5% Ru. In some embodiments, the composition comprises about 6% Ru. In some embodiments, the composition comprises about 7% Ru. In some embodiments, the composition comprises about 8% Ru. In some embodiments, the composition comprises about 9% Ru. In some embodiments, the composition comprises about 10% Ru.

In some embodiments, the composition comprises from about 50% to about 90% $SiO_2$. In some embodiments, the composition comprises at least about 90% $SiO_2$. In some embodiments, the composition comprises at least about 95% $SiO_2$. In some embodiments, the composition comprises about 90% $SiO_2$. In some embodiments, the composition comprises about 91% $SiO_2$. In some embodiments, the composition comprises about 92% $SiO_2$. In some embodiments, the composition comprises about 93% $SiO_2$. In some embodiments, the composition comprises about 94% $SiO_2$. In some embodiments, the composition comprises about 95% $SiO_2$. In some embodiments, the composition comprises about 96% $SiO_2$. In some embodiments, the composition comprises about 97% $SiO_2$. In some embodiments, the composition comprises about 98% $SiO_2$. In some embodiments, the composition comprises about 99% $SiO_2$. In some embodiments, the composition comprises about 99.5% $SiO_2$. In some embodiments, the composition comprises about 99.5% $SiO_2$. In some embodiments, the composition comprises about 99.9% $SiO_2$. In some embodiments, the composition comprises about 99.95% $SiO_2$.

In some embodiments, the composition comprises from about 50% to about 90% $TiO_2$. In some embodiments, the composition comprises at least about 90% $TiO_2$. In some embodiments, the composition comprises at least about 95% $TiO_2$. In some embodiments, the composition comprises about 90% $TiO_2$. In some embodiments, the composition comprises about 91% $TiO_2$. In some embodiments, the composition comprises about 92% $TiO_2$. In some embodiments, the composition comprises about 93% $TiO_2$. In some embodiments, the composition comprises about 94% $TiO_2$. In some embodiments, the composition comprises about 95% $TiO_2$. In some embodiments, the composition comprises about 96% $TiO_2$. In some embodiments, the composition comprises about 97% $TiO_2$. In some embodiments, the composition comprises about 98% $TiO_2$. In some embodiments, the composition comprises about 99% $TiO_2$. In some embodiments, the composition comprises about 99.5% $TiO_2$. In some embodiments, the composition comprises about 99.5% $TiO_2$. In some embodiments, the composition comprises about 99.9% $TiO_2$. In some embodiments, the composition comprises about 99.95% $TiO_2$.

In some embodiments, the composition comprises from about 50% to about 90% $ZrO_2$. In some embodiments, the composition comprises at least about 90% $ZrO_2$. In some embodiments, the composition comprises at least about 95% $ZrO_2$. In some embodiments, the composition comprises about 90% $ZrO_2$. In some embodiments, the composition comprises about 91% $ZrO_2$. In some embodiments, the composition comprises about 92% $ZrO_2$. In some embodiments, the composition comprises about 93% $ZrO_2$. In some embodiments, the composition comprises about 94% $ZrO_2$. In some embodiments, the composition comprises about 95% $ZrO_2$. In some embodiments, the composition comprises about 96% $ZrO_2$. In some embodiments, the composition comprises about 97% $ZrO_2$. In some embodiments, the composition comprises about 98% $ZrO_2$. In some embodiments, the composition comprises about 99% $ZrO_2$. In some embodiments, the composition comprises about 99.5% $ZrO_2$. In some embodiments, the composition comprises about 99.5% $ZrO_2$. In some embodiments, the composition comprises about 99.9% $ZrO_2$. In some embodiments, the composition comprises about 99.95% $ZrO_2$.

In some embodiments, the composition comprises from about 50% to about 90% $Al_2O_3$. In some embodiments, the composition comprises at least about 90% $Al_2O_3$. In some embodiments, the composition comprises at least about 95% $Al_2O_3$. In some embodiments, the composition comprises about 90% $Al_2O_3$. In some embodiments, the composition comprises about 91% $Al_2O_3$. In some embodiments, the composition comprises about 92% $Al_2O_3$. In some embodiments, the composition comprises about 93% $Al_2O_3$. In some embodiments, the composition comprises about 94% $Al_2O_3$. In some embodiments, the composition comprises about 95% $Al_2O_3$. In some embodiments, the composition comprises about 96% $Al_2O_3$. In some embodiments, the composition comprises about 97% $Al_2O_3$. In some embodiments, the composition comprises about 98% $Al_2O_3$. In some embodiments, the composition comprises about 99% $Al_2O_3$. In some embodiments, the composition comprises about 99.5% $Al_2O_3$. In some embodiments, the composition comprises about 99.5% $Al_2O_3$. In some embodiments, the composition comprises about 99.9% $Al_2O_3$. In some embodiments, the composition comprises about 99.95% $Al_2O_3$.

In some embodiments, the composition comprises from about 50% to about 90% Zeolite. In some embodiments, the composition comprises at least about 90% Zeolite. In some embodiments, the composition comprises at least about 95% Zeolite. In some embodiments, the composition comprises about 90% Zeolite. In some embodiments, the composition comprises about 91% Zeolite. In some embodiments, the composition comprises about 92% Zeolite. In some embodiments, the composition comprises about 93% Zeolite. In some embodiments, the composition comprises about 94% Zeolite. In some embodiments, the composition comprises about 95% Zeolite. In some embodiments, the composition comprises about 96% Zeolite. In some embodiments, the composition comprises about 97% Zeolite. In some embodiments, the composition comprises about 98% Zeolite. In some embodiments, the composition comprises about 99% Zeolite. In some embodiments, the composition comprises about 99.5% Zeolite. In some embodiments, the composition comprises about 99.5% Zeolite. In some embodiments, the composition comprises about 99.9% Zeolite. In some embodiments, the composition comprises about 99.95% Zeolite.

In some embodiments, the composition comprises about 99.95% SiO2 and about 0.5% Ag. In some embodiments, the composition comprises about 99.95% $SiO_2$ and about 0.5% Zn. In some embodiments, the composition comprises about 99% $SiO_2$ and about 1% Ag. In some embodiments, the composition comprises about 98% $SiO_2$ and about 2% Ag. In some embodiments, the composition comprises about 97% $SiO_2$ and about 3% Ag. In some embodiments, the composition comprises about 96% $SiO_2$ and about 4% Ag. In some embodiments, the composition comprises about 95% $SiO_2$ and about 5% Ag.

In some embodiments, the composition comprises about 99.92% $SiO_2$, about 0.5% Ag, and about 0.3% Zn. In some embodiments, the composition comprises about 98.7% $SiO_2$, about 1% Ag, and about 0.3% Zn. In some embodiments, the composition comprises about 97.7% $SiO_2$, about 2% Ag, and about 0.3% Zn. In some embodiments, the composition comprises about 96.7% $SiO_2$, about 3% Ag, and about 0.3% Zn. In some embodiments, the composition comprises about 95.7% $SiO_2$, about 4% Ag, and about 0.3% Zn, In some embodiments, the composition comprises about 94.7% $SiO_2$, about 5% Ag, and about 0.3% Zn. In some embodiments, the composition comprises about 92% $SiO_2$, about 5% Ag, and about 3% Zn.

In some embodiments, the composition comprises about 99.2% Zeolite, about 0.5% Ag, about 0.3% Zn, and about 0.3% Cu.

Silver and/or zinc can be in any form. In some embodiments, silver can be for example a colloid, a particle (e.g. a nanoparticle). In some embodiments, zinc can be for example a colloid, a particle (e.g. a nanoparticle).

In some embodiments, composition comprises at least a portion (e.g. at least 5%, at least 10%, at least 20%, at least 30%, at least 40%, at least 50%, at least 60%, at least 70%, at least 80%, at least 90%, at least 95%, 95% or more) of the silver or zinc on the surface of the matrix material. In some embodiments, the composition comprises at least a portion (e.g. at least 5%, at least 10%, at least 20%, at least 30%, at least 40%, at least 50%, at least 60%, at least 70%, at least 80%, at least 90%, at least 95%, 95% or more) of the silver or zinc is embedded within the matrix material.

Antimicrobial Activity

In some embodiment, a composition of the invention has antimicrobial activity. In some embodiments, the antimicrobial activity is an antibacterial activity. In some embodiments, the antimicrobial activity is an acaricidal activity. In some embodiments, the antimicrobial activity is an antiviral activity. In some embodiments, the antimicrobial activity is an antiparasitical activity. In some embodiments, the antimicrobial activity is an activity against other types of microorganisms.

Particles

In some embodiments, the composition is in the form of a particle. In some embodiments, the particle is a nanoparticle. In some embodiments, the particle has at least one dimension in the range of from about 0.1 nm to about 100 µm. In some embodiments, the particle has at least one dimension in the range of about 1 µm to about 10 µm.

In some embodiments, the matrix material is mesoporous. In some embodiments, the composition comprises at least 90% of the matrix material.

Without limitation, there are at least seven types of particles that can be formed by a composition described herein: (i) particles formed from a core formed by a matrix material, which core is coated with a molecule of interest, e.g., a metal material; (ii) particles formed from a core formed by a molecule of interest, e.g., a metal, which core is coated with a matrix material; (iii) particles formed from a generally homogenous mixture of a matrix material and a molecule of interest, e.g., a metal; (iv) particles formed from a core formed by a generally homogenous mixture of a molecule of interest, e.g., a metal, which core is coated with a molecule of interest, e.g., a metal; (v) particles formed from a core formed by a molecule of interest, e.g., a metal, which is core is coated with a generally homogenous mixture of a molecule of interest, e.g., a metal, and a matrix material; (vi) particles formed from a core formed by a non matrix material, which core is coated with a generally homogenous mixture of a matrix material and a molecule of interest, e.g., a metal; and (vii) particles formed from a core formed by a generally homogenous mixture, which core is coated with a non-matrix material.

As used herein, the term "particle" refers to any discrete unit of material structure. A particle can be of a defined shape, e.g., spheroid, ellipsoid, polygonal (where all sides can be same, all different, or some same and some different), cylindrical, disc like, prism like, and rod like, or can be of an irregular shape. Generally, a particle can range in size from 0.01 nm to 1000 µm.

In some embodiments, the composition of the invention is a particle. In some embodiments, the particle is a core shell particle. Particles that on the order to $10^{-6}$ to $10^{-3}$ of a meter is size are also referred to a microparticles herein. A microparticle can be of a defined shape, e.g., spheroid, ellipsoid, polygonal, cylindrical, disc like, prism like, and rod like, or can be of an irregular shape. The microparticles can be, e.g., monodisperse or polydisperse and the variation in diameter of the particles of a given dispersion may vary, e.g., particle diameters of between about 0.1 to 100's of µm. In some embodiments, a microparticle ranges in size from about 1 µm to about 1000 µm.

Particles that are on the order of $10^{-6}$ or one millionth of a meter and below in size are also referred to as nanoparticles herein. The term "nanoparticle" includes nanospheres; nanorods; nanoshells; and nanoprisms; and these nanoparticles may be part of a nanonetwork. The particles can be, e.g., monodisperse or polydisperse and the variation in diameter of the particles of a given dispersion may vary, e.g., particle diameters of between about 0.1 to 100's of nm. In some embodiments, a nanoparticle can range in size from about 0.1 nm to about 1000 nm.

Cleaning Compositions

One aspect of the invention relates to a cleaning composition comprising a composition of the invention. In some embodiments, the cleaning composition comprises nanoparticles. In some embodiments, the cleaning composition is used for cleaning and protecting surfaces with all the advantages of the prior art and the additional benefit of having an antimicrobial effect. In some embodiments, the cleaning composition has antibacterial activity. In some embodiments, the cleaning composition has acaricidal activity. In some embodiments, the cleaning solution has an antiviral activity. In some embodiments, the cleaning composition has an antiparasitical activity. In some embodiments, the cleaning composition is an activity against other types of microorganisms.

In some embodiments, the cleaning composition is a liquid. In some embodiments, the cleaning composition is a solid. In some embodiments, the cleaning composition is a powder. In some embodiments, the cleaning composition is a foam. In some embodiments, the cleaning composition is embedded in a support. In some embodiments, the support is styrofoam. In some embodiments, the cleaning composition is a gel. In some embodiments, the cleaning solution is an aqueous solution. N some embodiments, the cleaning solution is comprised in a time release system. In some embodiments, the cleaning solution is a concentrate that requires dilution before use.

A cleaning composition of the invention can be used to clean any type of surface, including but not limited to plastic, leather, vinyl, tiles, ceramic, marble, granite, stainless steel, paper, acrylic resin, food packaging, and composite materials. Additional examples of surfaces that can be clean using a cleaning composition of the invention include but are not limited to flooring, appliances, such as but not limited to kitchen appliances and cookware, medical and surgical apparatus and devices, cosmetic apparatus and devices such as comb, brushes, and sponges, textiles such as medical and surgical gowns and sheets, disposable and non-disposalable diapers and wipes, camping gear, furniture, such as but not limited to bed and spring boxes, bathrooms, carpets, rugs.

Polymeric Nanoparticle Stabilizer

In some embodiments, the composition comprises a polymeric stabilizer. In some embodiments, the polymeric stabilizer is a nanoparticle. Suitable nanoparticle stabilizer polymer should have a molecular weight of about 500 to about 1,000,000, more preferably from 1,000 to 200,000 especially from 5,000 to 100,000.

In some embodiments, the polymeric stabilizer is PMMA, PVA, PS, PEG, SAN, PP, PE, EVA, NR, PB, PA6, PET, PBT, PEO, or PU. In some embodiments, the polymeric stabilizer is an epoxy polymer. In some embodiments, the polymeric stabilizer is a phenolic polymer. In some embodiment, the polymeric stabilizer is PLA, PHB, or PCL. In some embodiments, the polymeric stabilizer is at least one of PMMA, PVA, PS, PEG, SAN, PP, PE, EVA, NR, PB, PA6, PET, PBT, PEO, PU, PLA, PHB, or PCL.

Nanoadditive/Nanofiller

One aspect of the invention relates to the composition of the invention as a nanoparticle. In some embodiments the nanoparticle is a nanofiller. In some embodiments, the nanoparticle is a nanoadditive.

Polymer

One aspect of the invention relates to the incorporation of a composition of the invention in a polymer. In some embodiments, the polymer is used for germicide for pool water, drinking water, and cooling water or slime control agent. In some embodiments, the polymer can be added to a synthetic resin and the like and can be used building materials, agricultural materials, etc. for example to prevent mold.

Resins

One aspect of the invention relates to the incorporation of a composition of the invention in resins. In some embodiments, the resin is a plastic resin.

In some embodiments, the composition comprises polymeric nanoparticles. In some embodiments, the polymeric nanoparticles are incorporated into a plastic resin. In some embodiments, the plastic resin exhibits higher antimicrobial activity.

In some embodiments, the resin is used in food packaging. In some embodiments, the food packaging is a food storage container, such as but not limited to bags, boxes, and tubs. In some embodiments, the food packaging is a beverage storage container.

In some embodiments, the resin is used in food handling. In some embodiments, the food handling is a plate, a cup, a utensil, a bowl, a fork, a knife, a spoon, an animal water dish.

In some embodiments, the composition of the invention does not discolor the resin. In some embodiments, the composition of the invention does not color the resin.

Ceramic Coatings

One aspect of the invention relates to ceramic coatings. Ceramic coatings are commonly used in products that store, treat, or transport water and liquid waste, or to prevent surface contamination. Ceramic toilets, urinals, bidets, bathroom basins, flooring tiles and other bathroom fixtures, hospital uses such as surfaces in surgical and infectious diseases units; public places such as airports and ground terminals are probably the most common example of such products.

Is some embodiments, the composition of the invention is incorporated in ceramic coating. In some embodiments, the invention relates to a ceramic article that exhibits antimicrobial properties. In some embodiments, the invention relates to a glazing composition comprising a composition of the invention. In some embodiments, the composition of the invention does not discolor the ceramic coating. In some embodiments, the composition of the invention does not color or discolor the ceramic coating.

Metal Coatings

One aspect of the invention relates to metal coatings. In some embodiments, the composition of the invention is incorporated in brass, bronze, chrome, steel, stainless steel, and antique finish metals. In some embodiments, the metal coating of the invention has enhanced antimicrobial properties. In some embodiments, the composition of the invention does not discolor the metal coating.

Textiles

One aspect of the invention relates to textiles. In some embodiments, the composition of the invention is incorporated in textile fabrics. In some embodiments, the textile is an antimicrobial textile. In some embodiments, the textile retains its antimicrobial properties upon washing.

In some embodiments, the invention can be described as any numbered paragraph:
1. A composition comprising a matrix material and both of silver and zinc distributed throughout, wherein the matrix material comprises at least one of $SiO_2$, $TiO_2$, $ZrO_2$, $Al_2O_3$, or Zeolite.
2. The composition of paragraph 1, wherein at least a portion of the silver or zinc is on the surface of the matrix material.
3. The composition of any one of paragraphs 1-2, wherein at least a portion of the silver or zinc is embedded within the matrix material.
4. The composition of any one of paragraphs 1-3, wherein the composition is a particle.
5. The composition of paragraph 4, wherein the particle is spheroid, prism, rod, disc, polygonal cylindrical, disc like, prism like, and rod like, or of an irregular shape.
6. The composition of any one of paragraphs 1-5, wherein the composition is a particle having at least one dimension in the range of from about 0.1 nm to about 100 μm.
7. The composition of paragraph 6, wherein the particle has at least one dimension in the range of about 1 μm to about 10 μm.
8. The composition of any one of paragraphs 1-7, wherein the matrix material is mesoporous.
9. The composition of any one of paragraphs 1-8, wherein the composition comprises at least 90% of the matrix material.
10. The composition of any one of paragraphs 1-9, wherein the silver or the zinc is in the form of a nanoparticle.
11. The composition of any one of paragraphs 1-9, wherein the silver or the zinc is in the form of a colloid.
12. The composition of any one of paragraphs 1-11, wherein the composition further comprises a metal selected from the group consisting of Cu, Pt, Rh, Ni, Co, Ru, and any combinations thereof.
13. The composition of any one of paragraphs 1-12, wherein the composition comprises from about 0.05% to about 10% of Ag.
14. The composition of any one of paragraphs 1-13, wherein the composition comprises from about 0.1% to about 5% of Ag.
15. The composition of any one of paragraphs 1-14, wherein the composition comprises from about 0.05% to about 10% of Zn.
16. The composition of any one of paragraphs 1-15, wherein the composition comprises from about 0.1% to about 5% of Zn.
17. The composition of any one of paragraphs 12-16, wherein the composition comprises from about 0.05% to about 10% of Cu.
18. The composition of any one of paragraphs 12-17, wherein the composition comprises from about 0.1% to about 5% of Cu.
19. The composition of any one of paragraphs 12-18, wherein the composition comprises from about 0.05% to about 10% of Pt.
20. The composition of any one of paragraphs 12-19, wherein the composition comprises from about 0.1% to about 5% of Pt.
21. The composition of any one of paragraphs 12-20, wherein the composition comprises from about 0.05% to about 10% of Rh.
22. The composition of any one of paragraphs 12-21, wherein the composition comprises from about 0.1% to about 5% of Rh.
23. The composition of any one of paragraphs 12-22, wherein the composition comprises from about 0.05% to about 10% of Ni.
24. The composition of any one of paragraphs 12-23, wherein the composition comprises from about 0.1% to about 5% of Ni
25. The composition of any one of paragraphs 12-24, wherein the composition comprises from about 0.05% to about 10% of Co.
26. The composition of any one of paragraphs 12-25, wherein the composition comprises from about 0.1% to about 5% of Co.
27. The composition of any one of paragraphs 12-26, wherein the composition comprises from about 0.05% to about 10% of Ru.
28. The composition of any one of paragraphs 12-27, wherein the composition comprises from about 0.1% to about 5% of Ru.
29. The composition of any one of paragraphs 1-28, wherein the composition comprises about 99.95% SiO2 and about 0.5% Ag.
30. The composition of any one of paragraphs 1-28, wherein the composition comprises about 99% $SiO_2$ and about 1% Ag.
31. The composition of any one of paragraphs 1-28, wherein the composition comprises about 98% $SiO_2$ and about 2% Ag.
32. The composition of any one of paragraphs 1-28, wherein the composition comprises about 97% $SiO_2$ and about 3% Ag.
33. The composition of any one of paragraphs 1-28, wherein the composition comprises about 96% $SiO_2$ and about 4% Ag.
34. The composition of any one of paragraphs 1-28, wherein the composition comprises about 95% $SiO_2$ and about 5% Ag.
35. The composition of any one of paragraphs 1-28, wherein the composition comprises about 99.95% $SiO_2$ and about 0.5% Zn.
36. The composition of any one of paragraphs 1-28, wherein the composition comprises about 99.92% $SiO_2$, about 0.5% Ag, and about 0.3% Zn.
37. The composition of any one of paragraphs 1-28, wherein the composition comprises about 98.7% $SiO_2$, about 1% Ag, and about 0.3% Zn.
38. The composition of any one of paragraphs 1-28, wherein the composition comprises about 97.7% $SiO_2$, about 2% Ag, and about 0.3% Zn.
39. The composition of any one of paragraphs 1-28, wherein the composition comprises about 96.7% $SiO_2$, about 3% Ag, and about 0.3% Zn.
40. The composition of any one of paragraphs 1-28, wherein the composition comprises about 95.7% $SiO_2$, about 4% Ag, and about 0.3% Zn,
41. The composition of any one of paragraphs 1-28, wherein the composition comprises about 94.7% $SiO_2$, about 5% Ag, and about 0.3% Zn.
42. The composition of any one of paragraphs 1-28, wherein the composition comprises about 92% $SiO_2$, about 5% Ag, and about 3% Zn.
43. The composition of any one of paragraphs 12-28, wherein the composition comprises about 99.2% Zeolite, about 0.5% Ag, about 0.3% Zn, and about 0.3% Cu.

44. The composition of any one of paragraphs 1-43, wherein the composition has antimicrobial activity.
45. A polymer composition comprising the composition of any one of paragraphs 1-44.
46. A molded article comprising the polymer of paragraph 45.
47. A nanofiller comprising the composition of anyone of paragraph 1-44.
48. A polymer comprising the nanofiller paragraph 47.
49. A ceramic coating comprising the composition of any one of paragraph 1-44.
50. A resin comprising the composition of any one of paragraph 1-44.
51. The resin of paragraph 50, wherein the resin is a plastic resin.
52. An antimicrobial composition comprising a composition of any one of paragraphs 1-44.
53. The antimicrobial composition of paragraph 36 further comprising an additive or a carrier.
54. A coating composition comprising a composition of any one of paragraphs 1-44.
55. A composite material comprising at least an outer layer comprising a composition of any one of paragraphs 1-44.
56. A composition comprising a matrix material, silver and at least one of the metal selected from the group consisting of the noble or transition metals distributed throughout, wherein the matrix material comprises at least one of $SiO_2$, $TiO_2$, $ZrO_2$, $Al_2O_3$, or Zeolite.
57. The composition of paragraph 56, wherein at least a portion of the silver or one of the metal selected from the group consisting of the noble or transition metals is on the surface of the matrix material.
58. The composition of any one of paragraphs 56-57, wherein at least a portion of the silver or one of the metal selected from the group consisting of the noble or transition metals is embedded within the matrix material.
59. The composition of any one of paragraphs 56-58, wherein the composition is a particle.
60. The composition of paragraph 59, wherein the particle is spheroid, prism, rod, disc, polygonal cylindrical, disc like, prism like, and rod like, or of an irregular shape.
61. The composition of any one of paragraphs 56-60, wherein the composition is a particle having at least one dimension in the range of from about 0.1 nm to about 100 μm.
62. The composition of paragraph 61, wherein the particle has at least one dimension in the range of about 1 μm to about 10 μm.
63. The composition of any one of paragraphs 56-62, wherein the matrix material is mesoporous.
64. The composition of any one of paragraphs 56-63, wherein the composition comprises at least 90% of the matrix material.
65. The composition of any one of paragraphs 56-64, wherein the silver or the one of the metal selected from the group consisting of the noble or transition metals is in the form of a nanoparticle.
66. The composition of any one of paragraphs 56-64, wherein the silver or the one of the metal selected from the group consisting of the noble or transition metals is in the form of a colloid.
67. The composition of any one of paragraphs 56-66, wherein the composition further comprises a metal selected from the group consisting of Cu, Pt, Rh, Ni, Co, Ru, and any combinations thereof.
68. The composition of any one of paragraphs 56-67, wherein the composition comprises from about 0.05% to about 10% of Ag.
69. The composition of any one of paragraphs 56-68, wherein the composition comprises from about 0.1% to about 5% of Ag.
70. The composition of any one of paragraphs 56-69, wherein the composition comprises from about 0.05% to about 10% of one of the metal selected from the group consisting of the noble or transition metals
71. The composition of any one of paragraphs 56-70, wherein the composition comprises from about 0.1% to about 5% of one of the metal selected from the group consisting of the noble or transition metals.
72. The composition of any one of paragraphs 68-71, wherein the composition comprises from about 0.05% to about 10% of Cu.
73. The composition of any one of paragraphs 68-72, wherein the composition comprises from about 0.1% to about 5% of Cu.
74. The composition of any one of paragraphs 68-73, wherein the composition comprises from about 0.05% to about 10% of Pt.
75. The composition of any one of paragraphs 68-74, wherein the composition comprises from about 0.1% to about 5% of Pt.
76. The composition of any one of paragraphs 68-75, wherein the composition comprises from about 0.05% to about 10% of Rh.
77. The composition of any one of paragraphs 68-76, wherein the composition comprises from about 0.1% to about 5% of Rh.
78. The composition of any one of paragraphs 68-77, wherein the composition comprises from about 0.05% to about 10% of Ni.
79. The composition of any one of paragraphs 68-78, wherein the composition comprises from about 0.1% to about 5% of Ni
80. The composition of any one of paragraphs 68-79, wherein the composition comprises from about 0.05% to about 10% of Co.
81. The composition of any one of paragraphs 68-80, wherein the composition comprises from about 0.1% to about 5% of Co.
82. The composition of any one of paragraphs 68-81, wherein the composition comprises from about 0.05% to about 10% of Ru.
83. The composition of any one of paragraphs 68-82, wherein the composition comprises from about 0.1% to about 5% of Ru.
84. The composition of any one of paragraphs 56-84, wherein the composition comprises about 99.95% $SiO_2$ and about 0.5% Ag.
85. The composition of any one of paragraphs 56-84, wherein the composition comprises about 99% $SiO_2$ and about 1% Ag.
86. The composition of any one of paragraphs 56-84, wherein the composition comprises about 98% $SiO_2$ and about 2% Ag.
87. The composition of any one of paragraphs 56-84, wherein the composition comprises about 97% $SiO_2$ and about 3% Ag.
88. The composition of any one of paragraphs 56-84, wherein the composition comprises about 96% $SiO_2$ and about 4% Ag.

89. The composition of any one of paragraphs 56-84, wherein the composition comprises about 95% $SiO_2$ and about 5% Ag.
90. The composition of any one of paragraphs 56-84, wherein the composition comprises about 99.95% $SiO_2$ and about 0.5% of one of the metal selected from the group consisting of the noble or transition metals.
91. The composition of any one of paragraphs 56-84, wherein the composition comprises about 99.92% $SiO_2$, about 0.5% Ag, and about 0.3% of one of the metal selected from the group consisting of the noble or transition metals.
92. The composition of any one of paragraphs 56-84, wherein the composition comprises about 98.7% $SiO_2$, about 1% Ag, and about 0.3% of one of the metal selected from the group consisting of the noble or transition metals.
93. The composition of any one of paragraphs 56-84, wherein the composition comprises about 97.7% $SiO_2$, about 2% Ag, and about 0.3% Zn.
94. The composition of any one of paragraphs 56-84, wherein the composition comprises about 96.7% $SiO_2$, about 3% Ag, and about 0.3% of one of the metal selected from the group consisting of the noble or transition metals.
95. The composition of any one of paragraphs 56-84, wherein the composition comprises about 95.7% $SiO_2$, about 4% Ag, and about 0.3% of one of the metal selected from the group consisting of the noble or transition metals.
96. The composition of any one of paragraphs 56-84, wherein the composition comprises about 94.7% $SiO_2$, about 5% Ag, and about 0.3% of one of the metal selected from the group consisting of the noble or transition metals.
97. The composition of any one of paragraphs 56-84, wherein the composition comprises about 92% $SiO_2$, about 5% Ag, and about 3% of one of the metal selected from the group consisting of the noble or transition metals.
98. The composition of any one of paragraphs 68-84, wherein the composition comprises about 99.2% Zeolite, about 0.5% Ag, about 0.3% of one of the metal selected from the group consisting of the noble or transition metals, and about 0.3% Cu.
99. The composition of any one of paragraphs 56-98, wherein the composition has antimicrobial activity.
100. A polymer composition comprising the composition of any one of paragraphs 56-99.
101. A molded article comprising the polymer of paragraph 100.
102. A nanofiller comprising the composition of anyone of paragraph 56-99.
103. A polymer comprising the nanofiller paragraph 102.
104. A ceramic coating comprising the composition of any one of paragraph 56-99.
105. A resin comprising the composition of any one of paragraph 56-99.
106. The resin of paragraph 105, wherein the resin is a plastic resin.
107. An antimicrobial composition comprising a composition of any one of paragraphs 56-99.
108. The antimicrobial composition of paragraph 107 further comprising an additive or a carrier.
109. A coating composition comprising a composition of any one of paragraphs 56-99.
110. A composite material comprising at least an outer layer comprising a composition of any one of paragraphs 56-99.

EXAMPLES

Example 1—Synthesis of an Antimicrobial Additive

The natural, silver-based antimicrobial nanoadditive was made by Nanox Technology S/A. Briefly, the silver nanoparticles were prepared by the wet chemistry method, first reducing silver to a colloid which was then anchored to silica by the metal impregnation on support method. Thirty liters of deionized water were heated to 80-90° C., and 0.5-5% of both silver and zinc nitrates were added to the solution. After that, 5 L of a solution of 1% of sodium citrate were then added. The resulting solution was stirred for 1 h, and then 10% w/w of silica and 65 L of water were added. After addition of silica, the reaction was stirred and heated for 90 minutes and then dried at 120° C., in furnace, for 12 hours. The starting silica has a surface area of 400 $m^2/g$ and a size particle around 5 microns. The concentration of silver in the silica surface can vary from 0.5% to 5% weight.

The structure and morphology of the silver-based nanoadditive produced as above were characterized by X-Ray diffraction and electronic microscopic scanning. The assessment of the toxicity was done by the methods described below.

Determination of the Acute Oral Toxicity (DLO) of the Silver Based Antimicrobial Additive The determination of the acute oral toxicity of the additive described above was done by the Medlab Scientific Analysis Laboratory Ltd., from São Paulo, SP, Brazil. Briefly, a single dose of 2000 mg/kg of body weight of the additive was orally administered to 3 adult Wistar albino rats (ratus norvergicus), age 4-6 weeks at the beginning of the study. The animals were then analyzed after a 24 hour period. The study was conducted according to OECD (Organization for Economic Co-operation for Development) 2001, n. 423. The additive has been classified by the GHCS—Global Harmonized Classification System, and its LD50 (median lethal oral dose) was determined based on the following a classification:

TABLE 1

Toxicity according to GHCS label

| Specification of the hazard | Category 1 | Category 2 | Category 3 | Category 4 | Category 5 |
|---|---|---|---|---|---|
| Death (animals) | 2-3 | 2-3 | 2-3 | 2-3 | 0-1 |
| Dose (mg/kg) Oral | 0-5 Fatal if swallowed | 5-50 Fatal if swallowed | 50-300 Toxic if swallowed | 300-2000 Harmful if swallowed | >2000 May be harmful if swallowed |

Example 2—Polymer Application

Production of Concentrate (Masterbatch)

The silver-based additive above was incorporated individually into several plastic resins, such as polystyrene (PS), polyethylene (PP), low density polyethylene (LDPE), ethylene terephthalate (PET) and others. The additive was homogenized in the resin with a twin-screw co-rotating extruder, for the production of the concentrate (the "masterbatch"), which contains 1.5% of the additive in the resin.

The final concentration of the masterbatch in the samples for the tests below was 1 to 5%, and the masterbatch performance was evaluated as follows.

Evaluation of Antimicrobial Activity

The efficacy of biocides incorporated in the plastics specimens was tested against known standards of *S. aureus* and *E. coli*. (JIS Z 2801:2000) by Bioagri Tests and Sanitary and Cosmetics Products Testing Ltd. (São Paulo, SP, Brazil).

Migration Assessment of the Additive in Packages

This assessment was required for regulatory approval of the silver-based nanoadditive for direct food contact in Brazil. CETEA Packaging Technology Center assessed the potential of migration of the silver in the polypropylene polymer, as compared to both the total and the specific migration of silver in food simulants. The test was conducted in according to the Resolution 105, May 19, 1999, published by the National Agency for Sanitary Surveillance of the Brazilian Ministry of Agriculture, published in the Official Gazette on May 20, 1999.

The samples for the migration assessment followed the classification below, which is used for foods and their simulants:

Type I: non-acid aqueous food (pH>5), for which distilled water is used as a simulant.

Type II: acid aqueous food (pH≤5), for which a solution of acetic acid in distilled water at 3% (w/v) is used as a simulant.

Type III a: non-acid aqueous foods containing fat or oil, for which distilled water and olive oil are used as simulants.

Type III b: acid aqueous foods containing fat or oil, for which a solution of acetic acid in water 3% (w/v) and olive oil are used as simulants.

Type IV: oily or fatty foods, for which olive oil is used as a simulant.

Type V: dry solid foods or foods with insignificant quarrying action. Migration assay not required.

Occasionally, it may be required to complete the migration test with distilled water, acetic acid 3% (w/v) or olive oil as simulants, depending on the type of food.

Acaricidal Activity

To further assess the biological effects of the silver-based nanoadditive, the acaricidal activity of samples of LDPE (low density polyethylene) with the silver-based antimicrobial, was evaluated by Prof. Dr. Claudette R. Paula, from the Department of Microbiology, Institute of Biomedical Sciences, University of São Paulo, São Paulo, SP, Brazil.

Approximately 100 adult mites of Dermatophagoides pteronyssinus were inoculated in Petri dishes (20×200 mm) with treated foam (3×3 cm), to which was added 0.25 gr of medium for the maintenance of live mites on the specimens of LDPE with silver-based natural antimicrobial additive. The additive was incorporated in the opposite sides of the mites in the dishes. The control was done with the foam without the test specimen.

Each sample was analyzed after 24 h of incubation at 25° C. The surviving mites were scored under 40× magnification at the end of each period. All tests were performed in triplicate.

For Ceramics and Tiles Application

The antimicrobial additive was incorporated into the glaze used for flooring tiles of houses, hospitals, etc., in the final stage of milling, at a concentration of 1 to 10% in the glaze. The additives used were 0.5% and 5% of silver in the silica surface. One hour grinding was necessary for the complete homogenization of the additives in the glaze. The glaze was then applied onto the ceramic tiles by spray or disc in the weight of 200 to 400 g/m2, followed by the same heat treatment curve used for untreated glazed tiles.

The samples were then submitted to the test to evaluate the efficacy of the biocides incorporated into ceramic glazes specimens, as compared to standard concentrations of *S. aureus* and *E. coli*, by standard methods (JIS Z 2801:2000 or ISO 22196-2007).

Study of Acute Oral Toxicity (DLO) of the Silver-Based Antimicrobial Additive

The natural antimicrobial additive was classified as Category 5 according to the adopted method and the established criteria (Table I). The LD50 was considered to be above 2000 mg/kg. Despite the high dose of the silver-based additive, no toxic effects were observed in the animals after administration of the additive.

Figure 1:
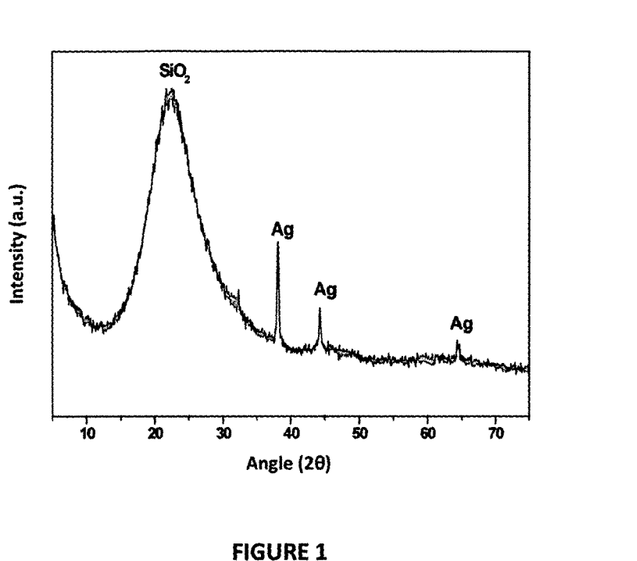
FIG. 1 represents the X-Ray profile of the silver-based antimicrobial additive.
Figure 2A:
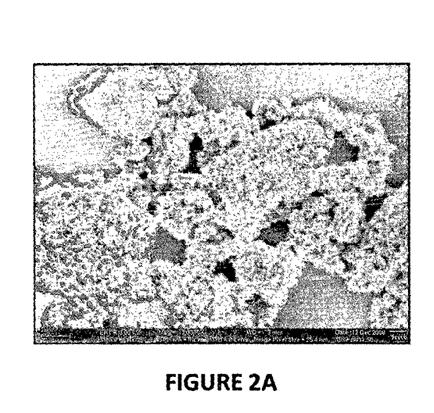
FIGS. 2A-2B illustrate a microstructure containing Ag, Zn, and $SiO_2$.
Figure 2B:
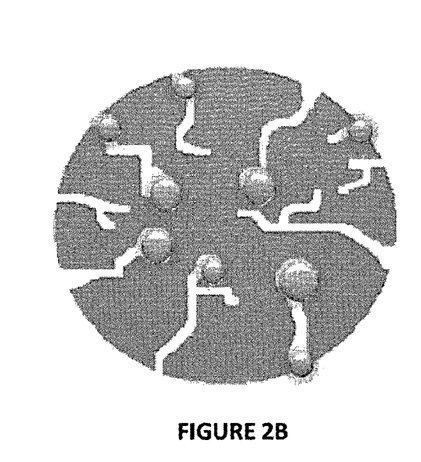
Figure 3A:
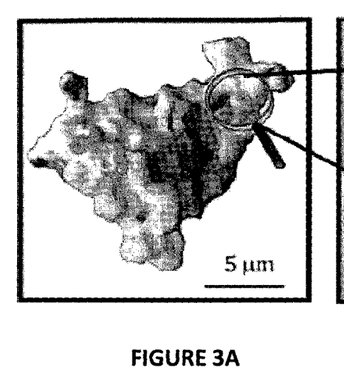
FIG. 3 illustrates the morphology and microstructure of an antimicrobial compound.
Figure 3B:
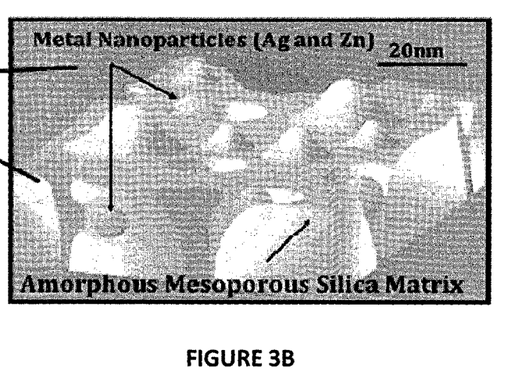

FIG. 1 represents the X-Ray profile of the silver-based antimicrobial additive ($SiO_2$—Ag—Zn). The main peak of the silver is close to 2 theta 39° and shows a compound with metallic silver nanoparticles, consistent with the expected complex between silver (Ag) and $SiO_2$. The diffraction peaks are consistent with $SiO_2$ and metallic silver. Other peaks of silver not complexed with $SiO_2$ are also seen, and are the expected Ag crystallographic peaks. FIG. 2A shows a SEM image of a sample with 0.5 wt % Ag and Zn, where the silver and zinc metals are dispersed on the $SiO_2$ matrix. FIG. 2B shows a schematic representation of the microstructure of the silver-based additive, with the metal nanoparticles dispersed on the $SiO_2$ matrix. The same metal nanoparticles are seen inside the silica pores. FIG. 3 illustrates the morphology and microstructure of the antimicrobial compounds. $SiO_2$ has a size particle of 5 microns, with silver and zinc islands on it.

Assessment of Antimicrobial Activity in Polymer Application

The silver-based nanoadditive is an effective bacteriostatic agent, as shown by a reduction greater than 99.999% of colony forming units (CFU), as compared to control, for all types of resins tested (PE, PP, PS and PET). The results are detailed in table 2.

TABLE 2

Viability of inoculum (control) and reduction percentage achieved in the samples tested after 24 hours of contact with the silver-based nanoadditive (average of duplicates).

| | | Microbial Bacteria Count (CFU/ml) | | | | | | | |
|---|---|---|---|---|---|---|---|---|---|
| | Control | Test Sample | | | | Reduction % Test Sample | | | |
| Bacteria | (Viability of the inoculum) | PEBD | PP | PS | PET | PEBD | PP | PS | PET |
| *S. aureus* | $3.3 \times 10^6$ | <10 | <10 | <10 | <10 | >99.999 | >99.999 | >99.999 | >99.999 |
| *E. coli* | $4.0 \times 10^6$ | <10 | <10 | <10 | <10 | >99.999 | >99.999 | >99.999 | >99.999 |

Assessment of Migration of the Additive in Packages a) Total Migration

Test results showing the total migration of PP (Polypropylene) in packaging incorporating the silver-based nanoadditive described above are shown in Table 3 below:

TABLE 3

Residue of total migration obtained for PP packaging with incorporated silver, mg/dm² [1].

| Simulants | Contact Condition | Average | Standard Deviation | Variation Interval |
|---|---|---|---|---|
| Distilled water | 40° C./10 days | ≤1.03[2] | [3] | [3] |
| Acetic acid solution in distilled water at 3% (w/v) | 40° C./10 days | 2.24 | 0.18 | 2.01-2.42 |
| Olive oil | 40° C./10 days | 4.17 | 1.16 | 3.38-6.03 |

[1] Results of four determinations
[2] Limit of quantification in the analytical conditions employed.
[3] Not applicable.

The maximum total migration established by Resolution no. 15/99 of the Brazilian legislation is 8 mg of residue/dm² of plastic material, with an analytical tolerance of 10%; therefore 8.8 mg/dm2 is the maximum tolerable migration.

The values of the total migration found in the sample with the silver-based nanoadditive, as compared to the simulants distilled water; acetic acid and 3% (w/v) and olive oil, in the experimental contact conditions used, were all below the maximum limit set.

b) Specific Migration of Metals

The results of specific migration of silver to the simulants distilled water and acetic acid 3% (w/v) are shown in table 4 below:

TABLE 4

Specific migration of silver in PP packaging with the natural antimicrobial additive incorporated in mg/kg of simulant [1].

| Simulants | Contact Condition | Average | Standard Deviation | Variation Interval |
|---|---|---|---|---|
| Distilled water | 40° C./10 days | ≤0.005[2] | [3] | [3] |
| Acetic acid solution m distilled water at 3% (w/v) | 40° C./10 days | ≤0.005[2] | [3] | [3] |

[1] Results of four determinations.
[2] Limit of quantification in the analytical conditions employed.
[3] Not applicable.

The total specific migration limit, SML (T), established for silver on the European, American and MERCOSUR legislations is 0.05 mg of silver per kilogram of simulant.

The values of specific migration of silver found in the analyzed samples for the simulants distilled water and acetic acid 3% (w/v), in the contact conditions used and described above, were all below the maximum limit set for silver.

Considering total migration, the PP packaging sample incorporating the silver-based additive showed levels lower than those that could restrict its use, including both food contact in general and contact with non-alcoholic beverages for extended use at up to 40° C. temperatures.

The packaging also showed values below 0.005 mg silver/kg of simulant for the silver specific migration. This value is below the specific migration limit set for silver by both Brazilian and international regulations.

Acaricidal Activity

Figure 4:
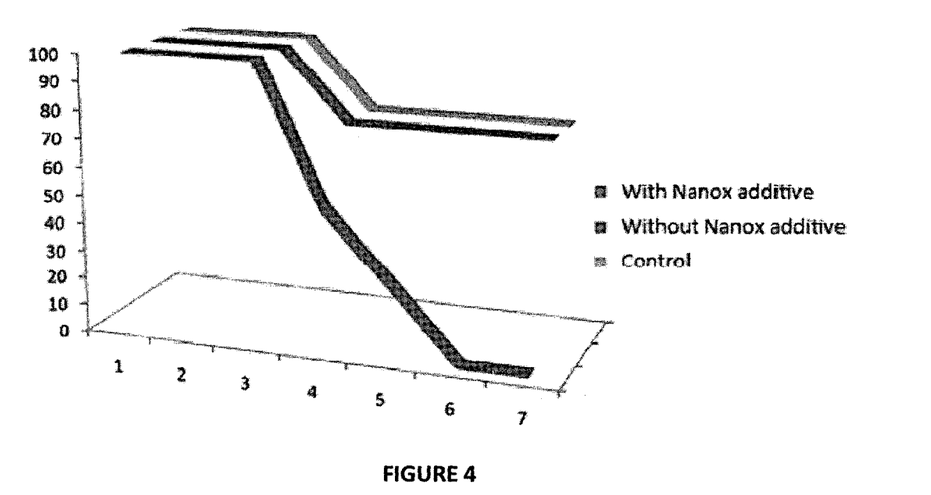
FIG. 4 represents a chart of the percentage of mite populations (y axis) versus days of exposure (x axis) in samples of polypropylene with incorporated antimicrobial silver-based nanoadditive; polypropylene without the antimicrobial additive incorporated, and a control sample.

The results of the acaricidal effect of the PP polypropylene sample with the natural silver-based nanoadditive are shown in Table 5 and FIG. 4.

Table 5 shows that the polypropylene with the nanoadditive sample did have acaricidal activity, under optimal conditions for the maintenance of the mites. The control board (CA) kept the mite populations in approximately 75% of inoculated mites.

TABLE 5

Results of the miticide action of the sample with silver incorporated polypropylene.

| | Mite population in the inoculated samples | | | | | | |
|---|---|---|---|---|---|---|---|
| Samples | Day 1 | Day 3 | Day 5 | Day 7 | Day 10 | Day 13 | Day 15 |
| with anti-microbial additive | ++++ | ++++ | ++++ | ++ | + | − | − |
| without anti-microbial additive | ++++ | ++++ | ++++ | +++ | +++ | +++ | +++ |
| CA | ++++ | ++++ | ++++ | ++++ | +++ | +++ | +++ |

CA = mite control growth without sample in the petri dish.
++++ = mite population of ±100 mites.
+++ = mite population of ±75 mites.
++ = mite population of ±50 mites.
+ = mite population of ±25 mites.
− = mite population of 0 mite.

The sample of polypropylene with the antimicrobial silver additive showed 100% acaricidal activity after 13 days, with dead mites in the sample of polypropylene with silver-based additive (Table 5). FIG. 4 illustrates the percentage of mite populations (y axis) versus days of exposure (x axis) in samples of polypropylene with incorporated antimicrobial silver-based nanoadditive; polypropylene without the antimicrobial additive incorporated, and the control sample.

For Ceramics and Tiles Application

Antimicrobial tests done in the ceramic samples with the nanoadditive are showed below:

TABLE 6

Viability of inoculum (control) and reduction percentage achieved in the samples tested after 24 hours of contact (average of duplicates) to samples with 50 ppm of Ag.

| Bacteria | Control (Viability of the inoculum) | Microbial Bacteria Count (CFU/ml) | Reduction % |
|---|---|---|---|
| S. aureus | $2.7 \times 10^5$ | 800 | 99.97 |
| E. coli | $1.8 \times 10^5$ | $1.6 \times 10^4$ | 91.11 |

TABLE 7

Viability of inoculum (control) and reduction percentage achieved in the samples tested after 24 hours of contact (average of duplicates) to samples with 100 ppm of Ag.

| Bacteria | Control (Viability of the inoculum) | Microbial Bacteria Count (CFU/ml) | Reduction % |
|---|---|---|---|
| S. aureus | $2.7 \times 10^5$ | 620 | 99.97 |
| E. coli | $1.8 \times 10^5$ | $1.3 \times 10^4$ | 92.77 |

TABLE 8

Viability of inoculum (control) and reduction percentage achieved in the samples tested after 24 hours of contact (average of duplicates) to samples with 500 ppm of Ag.

| Bacteria | Control (Viability of the inoculum) | Microbial Bacteria Count (CFU/ml) | Reduction % |
|---|---|---|---|
| S. aureus | $2.7 \times 10^5$ | 700 | 99.74 |
| E. coli | $1.8 \times 10^5$ | $2.4 \times 10^4$ | 86.66 |

TABLE 9

Viability of inoculum (control) and reduction percentage achieved in the samples tested after 24 hours of contact (average of duplicates) to samples with 1.000 ppm of Ag.

| Bacteria | Control (Viability of the inoculum) | Microbial Bacteria Count (CFU/ml) | Reduction % |
|---|---|---|---|
| S. aureus | $2.7 \times 10^5$ | 600 | 99.77 |
| E. coli | $1.8 \times 10^5$ | <10 | 100 |

The ceramic samples showed antimicrobial properties with silver concentration of 50 ppm, with the highest concentration of silver being able to eliminate 100% of bacteria.

What is claimed is:

1. A composition comprising a matrix material, silver and at least one other metal selected from the group consisting of noble or transition metals distributed throughout, wherein the matrix material comprises at least one of $SiO_2$, $TiO_2$, $ZrO_2$, $Al_2O_3$, or Zeolite, and wherein the composition is a particle having at least one dimension in the range of 1 μm to 100 μm, and wherein at least a portion of the silver and said at least one other metal selected from the group consisting of the noble or transition metals is on the surface of the matrix material, and at least a portion of the silver and said at least one other metal selected from the group consisting of the noble or transition metals is embedded within the matrix material.

2. The composition of claim 1, wherein the at least one other metal selected from the group consisting of the noble or transition metals is zinc.

3. The composition of claim 1, wherein the composition is free of a stabilizer.

4. The composition of claim 1, wherein the composition is a particle.

5. The composition of claim 1, wherein the composition is a particle having at least one dimension in the range of from about 1 μm to about 10 μm.

6. The composition of claim 1, wherein the composition comprises at least 90% of the matrix material.

7. The composition of claim 1, wherein the silver or the at least one other metal selected from the group consisting of the noble or transition metals is in the form of a nanoparticle or a colloid.

8. The composition of claim 1, wherein the at least one other metal is selected from the group consisting of Cu, Pt, Rh, Ni, Co, Ru, and any combinations thereof.

9. The composition of claim 8, wherein the composition comprises from about 0.05% to about 10% of Cu, Pt, Rh, Ni, Co, or Ru.

10. The composition of claim 1, wherein amount of Ag or the at least one other metal selected from the group consisting of the noble or transition metals is from about 0.05% to about 10%.

11. The composition of claim 1, wherein the composition comprises from about 99.92% $SiO_2$, about 0.5% Ag, and about 0.3% of said at least one other metal selected from the group consisting of the noble or transition metals; about 98.7% $SiO_2$, about 1% Ag, and about 0.3% of said at least one other metal selected from the group consisting of the noble or transition metals; about 97.7% $SiO_2$, about 2% Ag, and about 0.3% Zn; about 96.7% $SiO_2$, about 3% Ag, and about 0.3% of said at least one other metal selected from the group consisting of the noble or transition metals; about 95.7% $SiO_2$, about 4% Ag, and about 0.3% of said at least one other metal selected from the group consisting of the noble or transition metals; about 94.7% $SiO_2$, about 5% Ag, and about 0.3% of said at least one other metal selected from the group consisting of the noble or transition metals; about 92% $SiO_2$, about 5% Ag, and about 3% of said at least one other metal selected from the group consisting of the noble or transition metals; or about 99.2% Zeolite, about 0.5% Ag, about 0.3% of said at least one other metal selected from the group consisting of the noble or transition metals, and about 0.3% Cu.

12. The composition of claim 1, wherein the composition has antimicrobial activity.

13. A polymer composition comprising the composition of claim 1.

14. A nanofiller comprising the composition of claim 1.

15. A ceramic coating comprising the composition claim 1.

16. A resin comprising the composition of claim 1.

17. An antimicrobial composition comprising the composition of claim 1.

18. A coating composition comprising the composition of claim 1.

19. A composite material comprising at least an outer layer comprising the composition of claim 1.

20. The resin of claim 16, wherein the resin is a plastic resin.

21. The resin of claim 16, wherein the resin comprises polypropylene (PP), polypropylene polymer, polystyrene (PS), polyethylene (PE), low density polyethylene (LDPE), or ethylene terephthalate (PET).

22. The composition of claim 1, wherein the matrix material is mesoporous.

23. A food packaging container comprising the composition of claim 1.

24. The food packaging container of claim 23, wherein the food packaging container is selected from the group consisting of bags, boxes and tubs.

25. The food packaging container of claim 23, wherein the food packaging container is a beverage storage container.

26. A food handling article comprising the composition of claim 1.

27. The food handling article of claim 26, wherein the article is selected from the group consisting of a plate, a cup, a utensil, a bowl, a fork, a knife, a spoon, and an animal water dish.

28. A composition comprising a matrix material, silver and at least one other metal selected from the group consisting of noble or transition metals distributed throughout, wherein the matrix material comprises at least one of $SiO_2$, $TiO_2$, $ZrO_2$, $Al_2O_3$, or Zeolite, and wherein the composition is free of a stabilizer.

* * * * *